(12) United States Patent
Min et al.

(10) Patent No.: US 12,721,739 B2
(45) Date of Patent: Sep. 1, 2026

(54) ROBOTIC PROSTHETIC FOOT HAVING ELASTIC BODY

(71) Applicant: HUGO DYNAMICS, Daegu (KR)

(72) Inventors: Sung Joon Min, Yongin-si (KR); Byung Chae Kim, Yongin-si (KR); Kwon Mo Mun, Hongseong-gun (KR); Keun Jinn Kang, Daegu (KR); Wan Sue Choi, Anyang-si (KR)

(73) Assignee: HUGO DYNAMICS, Daegu (KR)

( * ) Notice: Subject to any disclaimer, the term of this patent is extended or adjusted under 35 U.S.C. 154(b) by 600 days.

(21) Appl. No.: 18/270,448

(22) PCT Filed: Dec. 21, 2021

(86) PCT No.: PCT/KR2021/019502
§ 371 (c)(1),
(2) Date: Jun. 29, 2023

(87) PCT Pub. No.: WO2022/145853
PCT Pub. Date: Jul. 7, 2022

(65) Prior Publication Data

US 2024/0065861 A1 Feb. 29, 2024

(30) Foreign Application Priority Data

Dec. 30, 2020 (KR) ........................ 10-2020-0187235

(51) Int. Cl.
*A61F 2/66* (2006.01)
*A61F 2/50* (2006.01)
*A61F 2/70* (2006.01)

(52) U.S. Cl.
CPC .................. *A61F 2/66* (2013.01); *A61F 2/70* (2013.01); *A61F 2002/5003* (2013.01); *A61F 2002/5009* (2013.01); *A61F 2002/701* (2013.01)

(58) Field of Classification Search
CPC ...... A61F 2/66; A61F 2/70; A61F 2002/5003; A61F 2002/5009; A61F 2002/701; A61F 2/50; A61F 2/60; A61F 2/6607
See application file for complete search history.

(56) References Cited

U.S. PATENT DOCUMENTS 5,957,981 A * 9/1999 Gramnas ............... A61F 2/6607 623/47
2022/0142793 A1 5/2022 Woo et al.

FOREIGN PATENT DOCUMENTS

KR 2000-0047310 A 7/2000
KR 2002-0002182 A 1/2002
(Continued)

OTHER PUBLICATIONS

KR Office Action dated Aug. 17, 2022 as received in Application No. 10-2020-0187235.
(Continued)

*Primary Examiner* — Yashita Sharma
(74) *Attorney, Agent, or Firm* — Maschoff Brennan

(57) ABSTRACT

A robotic prosthetic foot according to the present disclosure includes a coupling module having an upper portion to which a limb part of a user is coupled, a prosthetic foot module configured to be coupled to a lower portion of the coupling module and support a load of the user to enable the user to walk, and a joint module provided at the coupling module to enable the prosthetic foot module to rotate, wherein the joint module includes an elastic unit configured to compress and expand due to the prosthetic foot module rotating as the user walks and generate an elastic restoring force to facilitate the rotation of the prosthetic foot module.

8 Claims, 5 Drawing Sheets

(56) References Cited

FOREIGN PATENT DOCUMENTS

| | | | |
|---|---|---|---|
| KR | 10-2019-0025155 | A | 3/2019 |
| KR | 10-1994242 | B1 | 6/2019 |
| KR | 10-2020-0097169 | A | 8/2020 |

OTHER PUBLICATIONS

KR Office Action dated May 25, 2023 as received in Application No. 10-2020-0187235.

* cited by examiner

ROBOTIC PROSTHETIC FOOT HAVING ELASTIC BODY

TECHNICAL FIELD

The present disclosure relates to a robotic prosthetic foot having an elastic body, and more particularly, to a robotic prosthetic foot having an elastic body that allows smooth forward-backward rotation of a prosthetic foot module using an elastic restoring force of an elastic unit and, in a case in which a driving motor is provided, reduces a driving load of the driving motor using the elastic restoring force of the elastic unit.

BACKGROUND ART

With an increase in demand for robots that can perform dangerous tasks in the place of humans and prosthetic feet that can replace human feet, appropriate torque generation and weight have become important for performance of basic joint devices for supporting the weight and load and maintaining balance.

Prosthetic feet commercialized at an early stage were mostly developed to substitute for an amputated body part for an aesthetic purpose, but eventually, prosthetic feet that play important roles also in terms of functionality and enable natural walking and prevent excessive metabolic consumption of a user were developed.

However, for natural walking, torque for the walking propulsion should be sufficiently generated, and there is a problem that conventional robotic prosthetic feet are lightweight but have a difficulty outputting high torque.

In the related art, Korean Patent Document No. 10-1994242 discloses a method of using an elastic unit and a wire unit to improve torque output while reducing a load of a joint driving motor by an elastic restoring force of the elastic unit in order to improve torque output.

However, in the related art, compression and expansion of a robotic prosthetic foot are performed by connecting a wire to an elastic member such as a compression spring formed in a linear shape, and as a result, a stroke of the elastic unit is long which is inefficient, the volume of the robotic prosthetic foot is large, and the outer shape and structure of the robotic prosthetic foot are also complex, and the provided robotic prosthetic foot is not lightweight or compact.

Therefore, there is a need for a method of addressing the above problems.

DISCLOSURE

Technical Problem

The present disclosure is directed to providing a robotic prosthetic foot in which a radial arc-shaped elastic body is provided at a joint module configured to rotate a prosthetic foot module, and an elastic restoring force generated from the elastic body coincides with a rotating shaft of the joint module, thus allowing efficient rotation of the prosthetic foot module while having a lightweight and compact structure.

Also, the present disclosure is directed to providing a robotic prosthetic foot capable of, in a case in which a driving motor configured to transmit rotary power to the joint module is provided, reducing a driving load of the driving motor using an elastic restoring force of an elastic body.

Objectives of the present disclosure are not limited to those mentioned above, and other unmentioned objectives should be clearly understood by those of ordinary skill in the art from the description below.

Technical Solution

The present disclosure provides a robotic prosthetic foot having an elastic body, the robotic prosthetic foot including a coupling module having an upper portion to which a limb part of a user is coupled, a prosthetic foot module configured to be coupled to a lower portion of the coupling module and support a load of the user to enable the user to walk, and a joint module provided at the coupling module to enable the prosthetic foot module to rotate, wherein the joint module includes an elastic unit configured to compress and expand due to the prosthetic foot module rotating as the user walks and generate an elastic restoring force to facilitate the rotation of the prosthetic foot module.

Here, the joint module may include a case unit having one side coupled to the coupling module and the other side to which the prosthetic foot module is rotatably coupled, a hinge unit provided inside the case unit and configured to rotate in both directions to enable the prosthetic foot module to rotate, and a fixing unit provided outside the case unit to fix the elastic unit.

Also, the joint module may further include a guide unit having one side coupled to one side of the hinge unit and the other side coupled to one side of the prosthetic foot module so that a rotational force of the hinge unit is transmitted to the prosthetic foot module.

Also, the fixing unit may include a first fixing portion provided at a front of the case unit based on a rotating direction of the prosthetic foot module and a second fixing portion provided at a rear of the case unit based on the rotating direction of the prosthetic foot module.

Here, the elastic unit may include a first elastic body having one side fitted and coupled to the first fixing portion and a second elastic body having one side fitted and coupled to the second fixing portion.

Here, the first elastic body and the second elastic body may be spaced a predetermined distance apart from each other about the hinge unit and form an arc shape provided along an outer side surface of the case unit.

Also, the prosthetic foot module may include a first fitting portion configured to correspond to the first fixing portion and have one side of the first elastic body fitted and coupled thereto and a second fitting portion configured to correspond to the second fixing portion and have one side of the second elastic body fitted and coupled thereto.

Here, while the user wearing the robotic prosthetic foot walks, in a case in which the prosthetic foot module rotates forward, the first elastic body having one side fitted and coupled to the first fixing portion and the other side fitted and coupled to the first fitting portion may be compressed, and when the prosthetic foot module rotates backward, the compressed first elastic body may expand again, and an elastic restoring force may be generated and allow the user to continue walking smoothly.

Also, while the user wearing the robotic prosthetic foot walks, in a case in which the prosthetic foot module rotates backward, the second elastic body having one side fitted and coupled to the second fixing portion and the other side fitted and coupled to the second fitting portion may be compressed, and when the prosthetic foot module rotates forward, the compressed second elastic body may expand again, and an elastic restoring force may be generated and allow the user to continue walking smoothly.

Here, the robotic prosthetic foot may further include a driving motor which is provided inside the coupling module and able to be linked to the joint module to, in the joint module, generate power necessary to rotate the prosthetic foot module, and a driving load of the driving motor may be reduced due to the elastic restoring force of the elastic unit.

Advantageous Effects

A robotic prosthetic foot having an elastic body according to the present disclosure has the following advantageous effects.

First, since an elastic unit is provided, there is an advantage that, when a prosthetic foot module rotates, an elastic restoring force is generated, and forward-backward rotation of the prosthetic foot module can be smoothly performed.

Second, since the elastic unit is provided in a radial arc shape at a joint module, there are advantages that a stroke of the elastic unit can be minimized to minimize the volume, thus forming a compact structure, and the elastic restoring force generated from the elastic unit coincides with a rotating shaft of the joint module and maximizes efficiency of the elastic unit.

Third, since the elastic unit and the joint module are provided inside the robotic prosthetic foot, there is an advantage that the elastic unit and the joint module can be protected from external impact, thus extending the service life of the elastic unit and the joint module.

Advantageous effects of the present disclosure are not limited to those mentioned above, and other unmentioned advantageous effects should be clearly understood by those of ordinary skill in the art from the claims below.

DESCRIPTION OF REFERENCE NUMERALS

Figure 1:
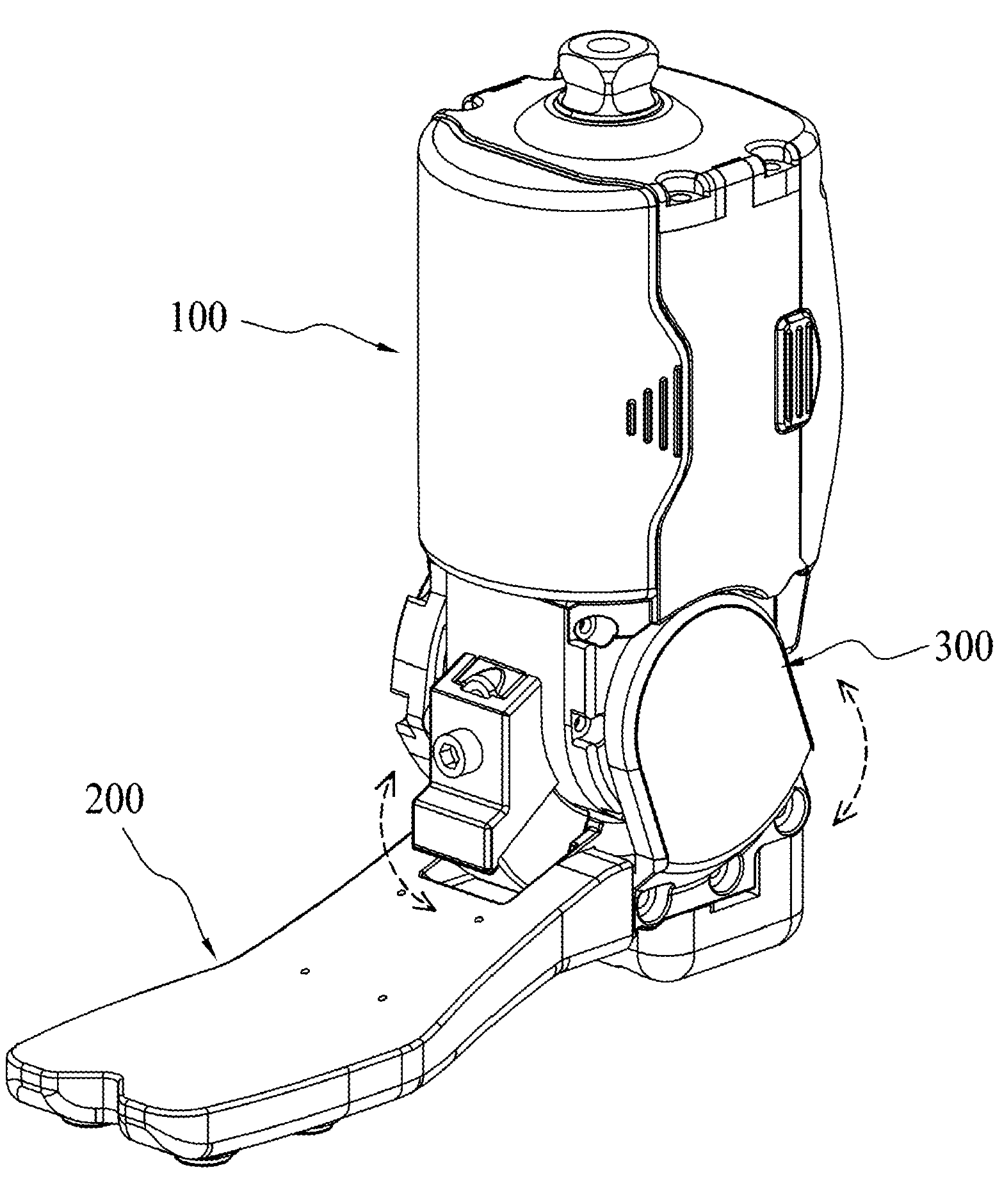
FIG. 1 is a perspective view illustrating a robotic prosthetic foot having an elastic body according to an embodiment of the present disclosure.

| | |
|---|---|
| 100: coupling module | 200: prosthetic foot module |
| 210: first fitting portion | 220: second fitting portion |
| 300: joint module | 310: elastic unit |
| 311: first elastic body | 312: second elastic body |
| 320: case unit | 330: hinge unit |
| 340: fixing unit | 341: first fixing portion |

-continued

| | |
|---|---|
| 342: second fixing portion | 350: guide unit |
| 400: driving motor | |

MODES OF THE INVENTION

Hereinafter, exemplary embodiments of the present disclosure by which the objectives of the present disclosure can be realized in detail will be described with reference to the accompanying drawings. In describing the present embodiments, the same configurations are referred to and denoted by the same names and the same reference numerals, and additional description thereof will be omitted.

Figure 2:
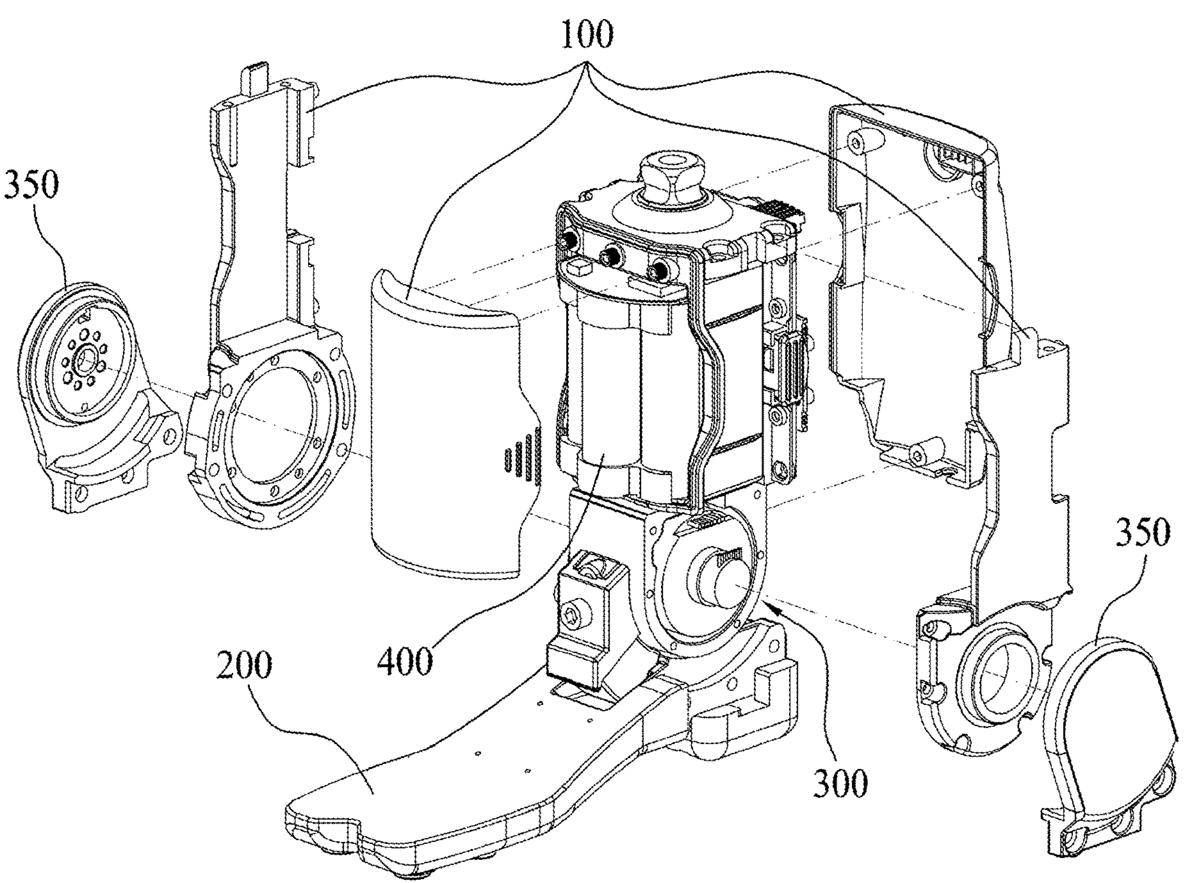
FIG. 2 is an exploded perspective view illustrating the robotic prosthetic foot having the elastic body according to an embodiment of the present disclosure.

The present disclosure relates to a robotic prosthetic foot having an elastic body that allows smooth forward-backward rotation of a prosthetic foot module using an elastic restoring force of an elastic unit and, in a case in which a driving motor is provided, reduces a driving load of the driving motor using the elastic restoring force of the elastic unit. As illustrated in FIGS. 1 and 2, the robotic prosthetic foot may include a coupling module 100 having an upper portion to which a limb part of a user is coupled, a prosthetic foot module 200 configured to be coupled to a lower portion of the coupling module 100 and support a load of the user to enable the user to walk, and a joint module 300 provided at the coupling module 100 to enable the prosthetic foot module 200 to rotate.

According to one embodiment of the present disclosure, a socket may be coupled to the upper portion of the coupling module 100, and the limb part of the user may be coupled to the socket to allow the user to wear the robotic prosthetic foot.

Also, the coupling module 100 may be formed of a single hollow structure but is not limited thereto and may be formed of a structure in which both side surfaces and front/rear surfaces are separately formed and coupled.

For example, the coupling module 100 may be formed in a single integrated shape or formed of a structure in which brackets for different portions are provided and coupled to form both side surfaces and front/rear surfaces, and in a case in which a driving motor 400, which will be described below, is provided inside the coupling module 100, the coupling module 100 may be formed of a structure in which brackets for different portions are coupled to an outer side surface of the driving motor 400 to surround both side surfaces and front/rear surfaces based on the driving motor 400, the brackets may be coupled so that the inside of the coupling module 100 is hollow, or the driving motor 400 may be provided inside the coupling module 100 formed as one body.

Here, the coupling module 100 may be formed of a structure whose one side may be opened and closed to facilitate the replacement and maintenance management of the driving motor 400.

Also, the joint module 300 which enables the prosthetic foot module 200 to rotate is provided at the coupling module 100 and is coupled and supported so that both side surfaces excluding front/rear surfaces are surrounded by the coupling module 100. In this way, the forward-backward rotation of the joint module 300 may be facilitated, and due to the forward-backward rotation of the joint module 300, the forward-backward rotation of the prosthetic foot module 200 coupled to the lower portion of the coupling module 100 may be facilitated.

Here, although not illustrated in detail, the coupling module 100, the joint module 300, and the prosthetic foot module 200 may be linked to each other and include various configurations for enabling rotation of the prosthetic foot module 200 by the joint module 300 so that the user wearing the robotic prosthetic foot can stably and smoothly walk.

Figure 3:
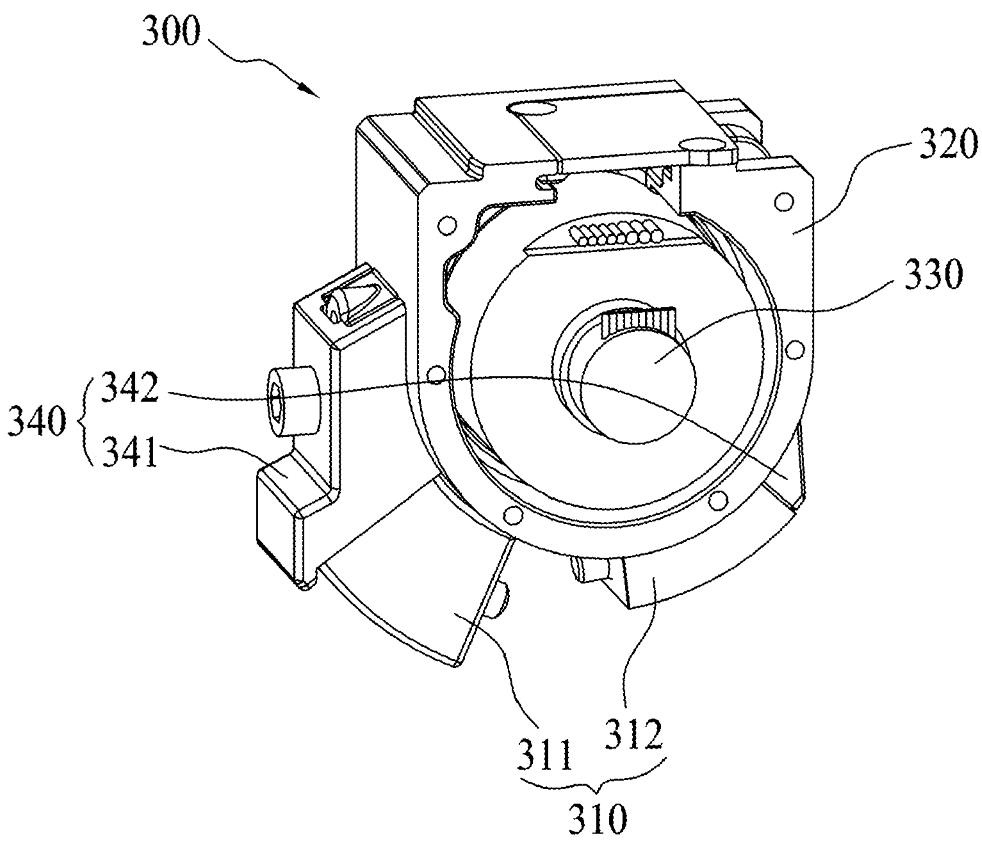
FIG. 3 is an exemplary diagram illustrating a joint module and an elastic unit in the robotic prosthetic foot having the elastic body according to an embodiment of the present disclosure.

According to one embodiment of the present disclosure, as illustrated in FIG. 3, the joint module 300 which may be provided at the coupling module 100 and enables the forward-backward rotation of the prosthetic foot module 200 coupled to the lower portion of the coupling module 100 may include an elastic unit 310 configured to further facilitate the rotation of the prosthetic foot module 200 by an elastic restoring force generated as the elastic unit 310 compresses and then expands according to the rotation of the prosthetic foot module 200.

Also, the joint module 300 may include a case unit 320 having one side coupled to the coupling module 100 and the other side to which the prosthetic foot module 200 is rotatably coupled, a hinge unit 330 provided inside the case unit 320 and configured to rotate in both directions to enable the prosthetic foot module 200 to rotate, and a fixing unit 340 provided outside the case unit 320 to fix the elastic unit 310.

Here, the case unit 320 has a flat upper surface and a D-shaped lower surface with a gentle slope, and in this way, the case unit 320 may be stably bound to the coupling module 100, and simultaneously, the prosthetic foot module 200 coupled to the lower portion of the coupling module 100 may easily reciprocate back and forth along the lower surface of the case unit 320.

Also, both side surfaces of the case unit 320 may be open, and a rotating shaft of the hinge unit 330 provided inside the case unit 320 is exposed to the outside.

Here, the joint module 300 may further include a guide unit 350 having one side coupled to one side of the hinge unit 330 and the other side coupled to one side of the prosthetic foot module 200 so that a rotational force of the hinge unit 330 is transmitted to the prosthetic foot module 200.

For example, the guide unit 350 may have one side coupled to one side of the hinge unit 330, in other words, the rotating shaft of the hinge unit 330 that is exposed to the outside through an open surface of the case unit 320, and may have the other side coupled to a side surface of the prosthetic foot module 200, and in this way, as the hinge unit 330 rotates, the guide unit 350 may rotate together, and simultaneously, the prosthetic foot module 200 coupled to the guide unit 350 may also rotate together.

The guide unit 350 may be provided as a pair of guide units 350 disposed at both sides of the hinge unit 330 and may allow the rotation of the prosthetic foot module 200 to be stably performed.

According to an embodiment of the present disclosure, the fixing unit 340 serves to fix the elastic unit 310, provided at the joint module 300 and configured to generate an elastic restoring force, and prevent the elastic unit 310 from being detached. The fixing unit 340 may be provided at one side of an outer side surface of the case unit 320 so that one side of the elastic unit 310 is fixed and may allow an elastic restoring force to be generated as the elastic unit 310 compresses and then expands again according to the rotation of the prosthetic foot module 200.

Here, the fixing unit 340 may be provided at each of both sides of the outer side surface of the case unit 320 based on a rotating direction of the prosthetic foot module 200 in order to appropriately correspond to two-way rotation of the prosthetic foot module 200 which can rotate both forward and backward.

For example, the fixing unit 340 may include a first fixing portion 341 provided at a front of the outer side surface of the case unit 320 based on the rotating direction of the prosthetic foot module 200 and a second fixing portion 342 provided at a rear of the outer side of the case unit 320 based on the rotating direction of the prosthetic foot module 200.

Also, the elastic unit 310, which has one side fixed to the fixing unit 340 and generates an elastic restoring force by compressing and then expanding again according to the rotation of the prosthetic foot module 200 to allow smooth forward-backward rotation of the prosthetic foot module 200, may also be provided as a pair of elastic units 310 to correspond to the fixing unit 340 made of the first fixing portion 341 and the second fixing portion 342.

For example, the elastic unit 310 may be provided as a pair of elastic units 310 including a first elastic body 311 having one side fitted and coupled to the first fixing portion 341 in order to be fixed and a second elastic body 312 having one side fitted and coupled to the second fixing portion 342 in order to be fixed.

Here, the first elastic body 311 and the second elastic body 312 constituting the elastic units 310 may be provided to be formed in a radial arc shape along a curved portion of the outer side surface of the case unit 320 whose lower portion has a D-shape with a circular edge, and in this way, an elastic restoring force may be generated in the same direction as a rotating shaft of the joint module 300, more specifically, a direction of axial rotation of the hinge unit 330, and the elastic restoring force may be generated most efficiently as the first elastic body 311 and the second elastic body 312 accurately compress and then expand again due to the rotation of the prosthetic foot module 200 rotating forward and backward due to the joint module 300.

For example, the first elastic body 311 and the second elastic body 312 may be provided at the front and rear based on the rotating direction of the prosthetic foot module 200 on the outer curved surface of the case unit 320 about the hinge unit 330 provided inside the case unit 320, and one side of the first elastic body 311 and one side of the second elastic body 312 may be coupled and fixed to one side of the first fixing portion 341 and one side of the second fixing portion 342, respectively.

More specifically, the first elastic body 311 and the second elastic body 312 may be provided at both front and rear sides based on the hinge unit 330, may be spaced a predetermined distance apart from each other, may be formed in an arc shape to correspond to the outer curved surface of the case unit 320, may be formed in the shape of a radial fan shape whose area progressively increases away from the center, and may accurately compress and expand due to movement of the prosthetic foot module 200 rotating forward and backward about the rotating shaft of the hinge unit 330, and in this way, efficiency of the elastic restoring force can be maximized.

For better understanding of the shapes of the first elastic body 311 and the second elastic body 312, for example, the shapes may be described as shapes of portions cut out from a donut.

Figure 4:
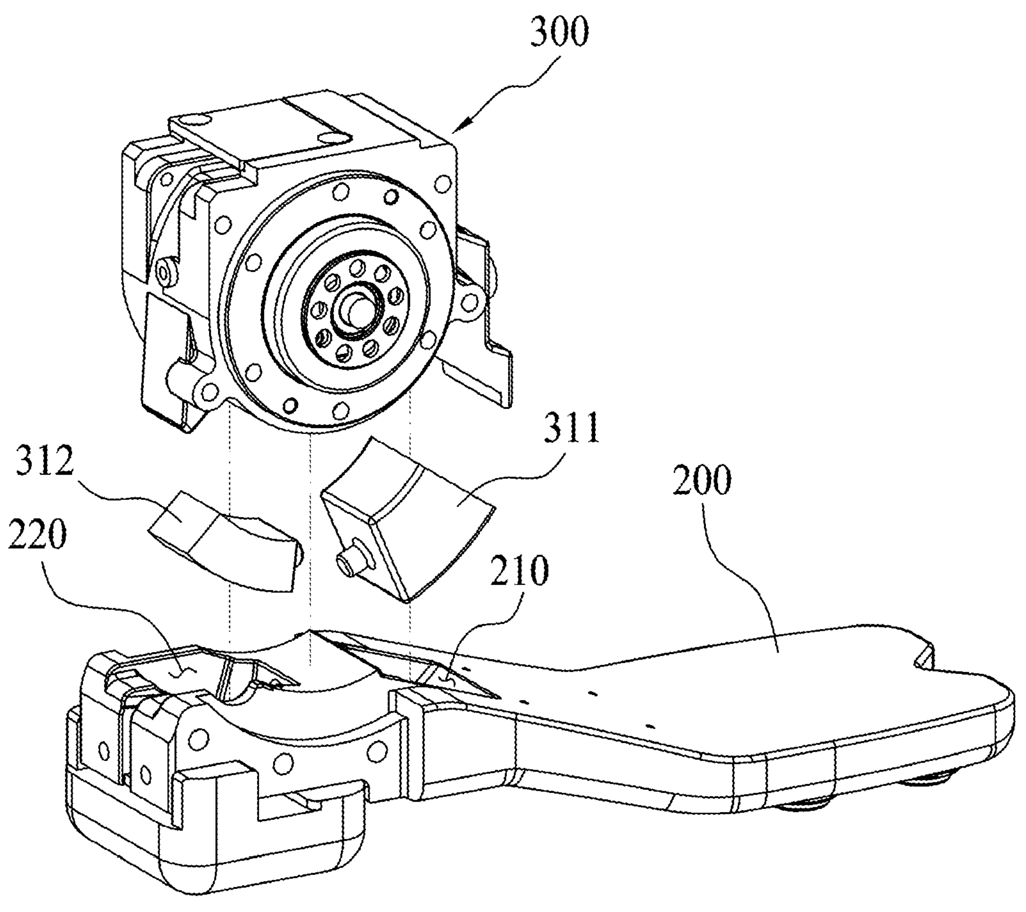
FIG. 4 is an exemplary diagram illustrating the coupling relationship of the joint module, the elastic unit, and a prosthetic foot module in the robotic prosthetic foot having the elastic body according to an embodiment of the present disclosure.

According to one embodiment of the present disclosure, as illustrated in FIG. 4, the prosthetic foot module 200 rotatably coupled to the joint module 300 and capable of reciprocating back and forth may have a coupling portion formed in a shape corresponding to the lower curved surface of the case unit 320 to enable one side of an upper end of the prosthetic foot module 200 to reciprocate back and forth along the outer side surface of the case unit 320 and may have a first fitting portion 210 and a second fitting portion 220 formed at both front and rear sides based on the coupling portion to allow each of the first elastic body 311 and the second elastic body 312 to be fixed.

In other words, in order to allow the first elastic body 311 and the second elastic body 312, which are fitted and fixed to the first fixing portion 341 and the second fixing portion 342 provided at the front and rear of the outer side of the case unit 320 based on the rotating direction of the prosthetic foot module 200 in the joint module 300, the first fitting portion 210 configured to correspond to the first fixing portion 341 and have one side of the first elastic body 311 fitted and coupled thereto and the second fitting portion 220 configured to correspond to the second fixing portion 342 and have one side of the second elastic body 312 fitted and coupled thereto may be formed at both front and rear sides based on the coupling portion at an upper portion of the prosthetic foot module 200.

Here, the first fitting portion 210 and the second fitting portion 220 may be formed in the shape of a groove that is recessed toward the inside of the prosthetic foot module 200 and may allow the first elastic body 311 and the second elastic body 312 to be supported by being fitted and coupled thereto. A coupling member or a fastening member, which allow the first fitting portion 210 and the first elastic body 311 to be coupled to each other and allow the second fitting portion 220 and the second elastic body 312 to be coupled to each other, may be provided to strengthen binding between the first fitting portion 210 and the first elastic body 311 and binding between the second fitting portion 220 and the second elastic body 312 in order to prevent the first fitting portion 210, the first elastic body 311, the second fitting portion 220, and the second elastic body 312 from being detached from fixed positions thereof while the first elastic body 311 and the second elastic body 312 repeat compression and expansion.

Figure 5A:
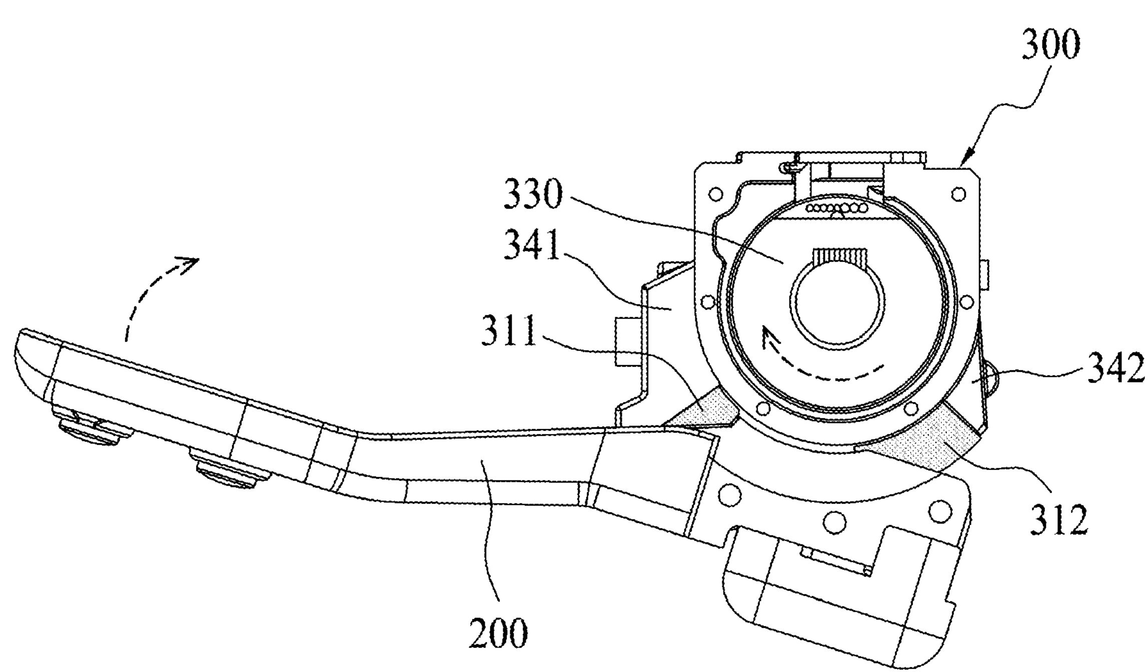
FIG. 5 is an exemplary diagram illustrating the elastic unit configured to generate an elastic restoring force according to rotation of the prosthetic foot module in the robotic prosthetic foot having the elastic body according to an embodiment of the present disclosure.
Figure 5B:
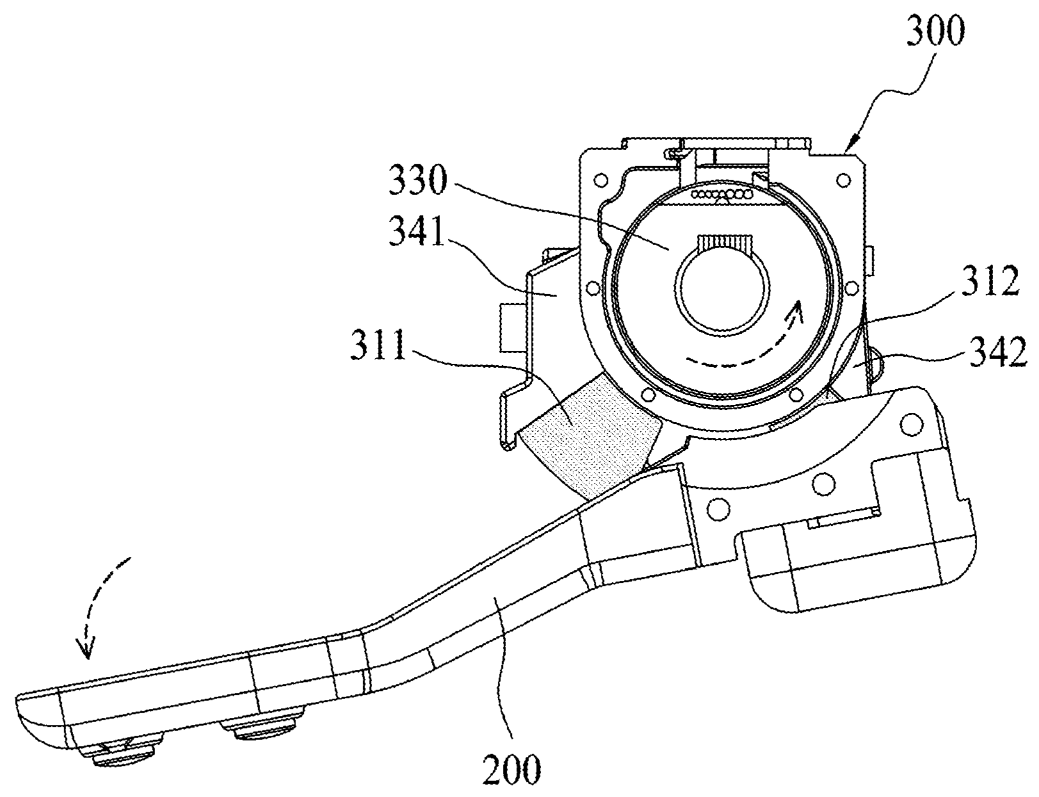

As illustrated in FIG. 5A, in the robotic prosthetic foot having the elastic body according to the present disclosure having the above-described structure, while the user wearing the robotic prosthetic foot walks, in a case in which the hinge unit 330 rotates and the prosthetic foot module 200 rotates forward, the first elastic body 311 having one side fitted and coupled to the first fixing portion 341 and the other side fitted and coupled to the first fitting portion 210 may be compressed, and when the hinge unit 330 rotates in the opposite direction and the prosthetic foot module 200 rotates backward, the compressed first elastic body 311 may expand again, and an elastic restoring force may be generated and allow the user to continue walking smoothly. Conversely, while the user wearing the robotic prosthetic foot walks, in a case in which the hinge unit 330 rotates and the prosthetic foot module 200 rotates backward, as illustrated in FIG. 5B, the second elastic body 312 having one side fitted and coupled to the second fixing portion 342 and the other side fitted and coupled to the second fitting portion 220 may be compressed, and when the hinge unit 330 rotates in the opposite direction and the prosthetic foot module 200 rotates forward, the compressed second elastic body 312 may expand again, and an elastic restoring force may be generated and allow the user to continue walking smoothly.

In this way, by the actions of the prosthetic foot module 200 reciprocating back and forth as the user walks and the first elastic body 311 and the second elastic body 312 repeatedly generating an elastic restoring force at the front and rear of the prosthetic foot module 200 corresponding to the movement of the prosthetic foot module 200, the user can walk naturally while exhaustion of the user's physical strength is minimized, and the load of the robotic prosthetic foot itself may be reduced, thus extending the service life of the robotic prosthetic foot.

According to one embodiment of the present disclosure, the robotic prosthetic foot may further include the driving motor 400 which can be provided inside the coupling module 100 and coupled to be linked to the joint module 300 to, in the joint module 300, generate power necessary to rotate the prosthetic foot module 200.

The driving motor 400 may serve to, while the user wearing the robotic prosthetic foot walks, further reduce exhaustion of the user's physical strength and further facilitate walking.

For example, a lower end of the driving motor 400, which can be provided inside the coupling module 100, and an upper end of the joint module 300 may be coupled to transmit power generated from the driving motor 400 to the joint module 300, and since two-way rotation of the hinge unit 330 is made possible by the power of the driving motor 400 in the joint module 300, the prosthetic foot module 200 connected to the joint module 300 may rotate both forward and backward.

Here, the elastic restoring force of the elastic unit 310 provided in the joint module 300 as described above may reduce a burden on the driving motor 400 rotating the hinge unit 330, and in this way, a driving load of the driving motor 400 may be reduced, and a driving life of the driving motor 400 may be extended.

Also, even in a case in which the driving motor 400 suddenly stops or a power module applying power necessary to drive the driving motor 400 is discharged while the user wearing the robotic prosthetic foot is walking, the elastic unit 310 generating the elastic restoring force in the same direction as the rotating shaft of the joint module 300 rotating the prosthetic foot module 200 as described above can still fulfill its role, thus allowing the user to stably walk.

Exemplary embodiments according to the present disclosure have been described above, and the fact that the present disclosure can be embodied in specific forms other than the above-described embodiments without departing from the gist or scope thereof should be apparent to those of ordinary skill in the art. Therefore, the above-described embodiments should be considered illustrative rather than limiting, and accordingly, the present disclosure is not limited to the above description and may be changed within the scope of the appended claims and the scope equivalent thereto.

INDUSTRIAL APPLICABILITY

According to the present disclosure, since an elastic unit is provided, when a prosthetic foot module rotates, an elastic restoring force is generated, and forward-backward rotation of the prosthetic foot module can be smoothly performed. Since the elastic unit is provided in a radial arc shape at a joint module, a stroke of the elastic unit can be minimized to minimize the volume, thus forming a compact structure, and the elastic restoring force coincides with a rotating shaft of the joint module and maximizes efficiency of the elastic unit. Since the elastic unit and the joint module are provided inside the robotic prosthetic foot, the elastic unit and the joint module can be protected from external impact, thus extending the service life of the elastic unit and the joint module. In this way, the present disclosure may be more effective in the field of robotic prosthetic feet.

The invention claimed is:

1. A robotic prosthetic foot having an elastic body, the robotic prosthetic foot comprising:

a coupling module having an upper portion to which a limb part of a user is coupled;

a prosthetic foot module configured to be coupled to a lower portion of the coupling module and support a load of the user to enable the user to walk; and a joint module provided at the coupling module to enable the prosthetic foot module to rotate, wherein the joint module includes:

an elastic unit configured to compress and expand due to the prosthetic foot module rotating as the user walks and generate an elastic restoring force to facilitate the rotation of the prosthetic foot module, a case unit having one side coupled to the coupling module and the other side to which the prosthetic foot module is rotatably coupled, a hinge unit provided inside the case unit and configured to rotate in both directions to enable the prosthetic foot module to rotate, and a fixing unit provided outside the case unit to fix the elastic unit, and wherein the fixing unit includes:

a first fixing portion provided at a front of the case unit based on a rotating direction of the prosthetic foot module, and a second fixing portion provided at a rear of the case unit based on the rotating direction of the prosthetic foot module.

2. The robotic prosthetic foot of claim 1, wherein the joint module further includes a guide unit having one side coupled to one side of the hinge unit and the other side coupled to one side of the prosthetic foot module so that a rotational force of the hinge unit is transmitted to the prosthetic foot module.

3. The robotic prosthetic foot of claim 1, wherein the elastic unit includes:

a first elastic body having one side fitted and coupled to the first fixing portion; and a second elastic body having one side fitted and coupled to the second fixing portion.

4. The robotic prosthetic foot of claim 3, wherein the first elastic body and the second elastic body are spaced a predetermined distance apart from each other about the hinge unit and form an arc shape provided along an outer side surface of the case unit.

5. The robotic prosthetic foot of claim 3, wherein the prosthetic foot module includes:

a first fitting portion configured to correspond to the first fixing portion and have one side of the first elastic body fitted and coupled thereto; and a second fitting portion configured to correspond to the second fixing portion and have one side of the second elastic body fitted and coupled thereto.

6. The robotic prosthetic foot of claim 5, wherein, while the user wearing the robotic prosthetic foot walks, in a case in which the prosthetic foot module rotates forward, the first elastic body having one side fitted and coupled to the first fixing portion and the other side fitted and coupled to the first fitting portion is compressed, and when the prosthetic foot module rotates backward, the compressed first elastic body expands again, and an elastic restoring force is generated and allows the user to continue walking smoothly.

7. The robotic prosthetic foot of claim 5, wherein, while the user wearing the robotic prosthetic foot walks, in a case in which the prosthetic foot module rotates backward, the second elastic body having one side fitted and coupled to the second fixing portion and the other side fitted and coupled to the second fitting portion is compressed, and when the prosthetic foot module rotates forward, the compressed second elastic body expands again, and an elastic restoring force is generated and allows the user to continue walking smoothly.

8. The robotic prosthetic foot of claim 1, further comprising a driving motor which is provided inside the coupling module and able to be linked to the joint module to, in the joint module, generate power necessary to rotate the prosthetic foot module, wherein a driving load of the driving motor is reduced due to the elastic restoring force of the elastic unit.

* * * * *